United States Patent
King et al.

(10) Patent No.: US 9,932,230 B2
(45) Date of Patent: Apr. 3, 2018

(54) CONVERSION OF GREENHOUSE GASES BY DRY REFORMING

(71) Applicant: ECOKAP TECHNOLOGIES LLC, Miami, FL (US)

(72) Inventors: Paul E. King, Albany, OR (US); Ben Zion Livneh, Denver, CO (US)

(73) Assignee: ECOKAP Technologies LLC, Miami, FL (US)

( * ) Notice: Subject to any disclaimer, the term of this patent is extended or adjusted under 35 U.S.C. 154(b) by 0 days.

(21) Appl. No.: 15/228,861

(22) Filed: Aug. 4, 2016

(65) Prior Publication Data
US 2017/0129777 A1  May 11, 2017

Related U.S. Application Data

(60) Provisional application No. 62/202,768, filed on Aug. 7, 2015.

(51) Int. Cl.
*C01B 3/38* (2006.01)
*C07B 41/02* (2006.01)
(Continued)

(52) U.S. Cl.
CPC ............ *C01B 3/384* (2013.01); *B01D 53/261* (2013.01); *B01D 53/265* (2013.01); *B01J 12/005* (2013.01);
(Continued)

(58) Field of Classification Search
CPC ............ C01B 3/384; C01B 2203/0238; C01B 2203/062; C01B 2203/0855;
(Continued)

(56) References Cited

U.S. PATENT DOCUMENTS

| 3,505,204 A | 4/1970 | Hoffman |
| 4,256,654 A | 3/1981 | Schlinger et al. |

(Continued)

FOREIGN PATENT DOCUMENTS

| CN | 101665721 | 3/2010 |
| GB | 2096635 | 10/1982 |

(Continued)

OTHER PUBLICATIONS

Zhang et a., process for producing synthetic gas by microwave rein forced methane and carbon dioxide reformation, English machine translation of CN1351953 A, Jun. 2002.*

(Continued)

*Primary Examiner* — Jafar Parsa
(74) *Attorney, Agent, or Firm* — David S. Alavi

(57) ABSTRACT

A method for conversion of greenhouse gases comprises: introducing a flow of a dehumidified gaseous source of carbon dioxide into a reaction vessel; introducing a flow of a dehumidified gaseous source of methane into the reaction vessel; and irradiating catalytic material in the reaction vessel with microwave energy. The irradiated catalytic material is heated and catalyzes an endothermic reaction of carbon dioxide and methane that produces hydrogen and carbon monoxide. At least a portion of heat required to maintain a temperature within the reaction vessel is supplied by the microwave energy. A mixture that includes carbon monoxide and hydrogen can undergo catalyzed reactions producing multiple-carbon reaction products in a lower-temperature portion of the reaction vessel.

21 Claims, 1 Drawing Sheet

(51) Int. Cl.
　　　B01D 53/26　　(2006.01)
　　　C07B 41/10　　(2006.01)
　　　C07B 41/08　　(2006.01)
　　　C07B 41/06　　(2006.01)
　　　C10G 2/00　　(2006.01)
　　　B01J 19/24　　(2006.01)
　　　B01J 19/02　　(2006.01)
　　　B01J 19/00　　(2006.01)
　　　B01J 12/00　　(2006.01)

(52) U.S. Cl.
　　　CPC ......... *B01J 12/007* (2013.01); *B01J 19/0006* (2013.01); *B01J 19/02* (2013.01); *B01J 19/245* (2013.01); *C07B 41/02* (2013.01); *C07B 41/06* (2013.01); *C07B 41/08* (2013.01); *C07B 41/10* (2013.01); *C10G 2/32* (2013.01); *B01J 2219/00164* (2013.01); *C01B 2203/0238* (2013.01); *C01B 2203/062* (2013.01); *C01B 2203/0855* (2013.01); *C01B 2203/0872* (2013.01); *C01B 2203/1241* (2013.01); *C01B 2203/1258* (2013.01); *C01B 2203/169* (2013.01)

(58) Field of Classification Search
　　　CPC .... C01B 2203/2203; C01B 2203/0872; C01B 2203/1241; C01B 2203/1258; C01B 2203/169; B01J 12/055; B01J 19/0006; B01J 19/02; B01J 19/245; C10G 2/32; C07B 41/02; C07B 41/06; C07B 41/08; C07B 41/10; B01D 53/261; B01D 53/265
　　　See application file for complete search history.

(56) References Cited

U.S. PATENT DOCUMENTS

| | | | |
|---|---|---|---|
| 4,435,374 | A | 3/1984 | Helm |
| 5,205,912 | A | 4/1993 | Murphy |
| 5,266,175 | A | 11/1993 | Murphy |
| 5,972,175 | A | 10/1999 | Tanner et al. |
| 7,887,694 | B2 | 2/2011 | Constantz et al. |
| 8,388,706 | B2 | 3/2013 | Ugolin |
| 8,779,013 | B2 | 7/2014 | Livneh |
| 9,238,214 | B2 | 1/2016 | Livneh |
| 9,353,323 | B2 | 5/2016 | Kyle |
| 2003/0162846 | A1 | 8/2003 | Wang et al. |
| 2004/0003173 | A1 | 2/2004 | Honeycutt et al. |
| 2004/0209303 | A1 | 10/2004 | Martin |
| 2007/0004809 | A1 | 1/2007 | Lattner et al. |
| 2009/0205254 | A1 | 8/2009 | Zhu et al. |
| 2010/0005720 | A1 | 1/2010 | Stadler et al. |
| 2010/0219107 | A1 | 1/2010 | Parsche |
| 2011/0126461 | A1 | 6/2011 | Bromberg et al. |
| 2012/0024843 | A1 | 2/2012 | Lissiaski et al. |
| 2012/0055851 | A1 | 3/2012 | Kyle |
| 2012/0311931 | A1 | 12/2012 | Dooher |
| 2013/0197288 | A1 | 8/2013 | Schafer et al. |
| 2013/0213795 | A1 | 8/2013 | Strohm et al. |
| 2013/0303637 | A1 | 11/2013 | Kyle |
| 2014/0051775 | A1 | 2/2014 | Kyle |
| 2014/0066526 | A1 | 3/2014 | Kyle |
| 2014/0163120 | A1 | 6/2014 | Kyle |
| 2014/0346030 | A1 | 11/2014 | Livneh |
| 2015/0246337 | A1 | 9/2015 | Hong et al. |
| 2016/0024405 | A1* | 1/2016 | Kyle ................ C10G 2/35 518/704 |
| 2016/0222300 | A1 | 8/2016 | Livneh |
| 2016/0333281 | A1 | 11/2016 | Kyle |

FOREIGN PATENT DOCUMENTS

| WO | WO 2008/009644 | 1/2008 |
|---|---|---|
| WO | WO 2014/038907 | 3/2014 |

OTHER PUBLICATIONS

Lavoie; "Review on dry reforming of methane . . . "; Frontiers in Chemistry vol. 2 Article 81 pp. 1-17; Nov. 11, 2014.
Fidalgo et al; "Microwave-assisted dry reforming of methane"; Intl. J. Hydrogen Energy vol. 22 p. 4337 (2008).
Fidalgo et al; "Syngas Production by CO2 Reforming of CH4 under Microwave Heating . . . "; Syngas Production, Application and Environmental Impact, Indarto and Palguandi Eds. p. 121 (2013).
Hunt et al; Microwave-Specific Enhancement of the Carbon-Carbon Dioxide (Boudouard) Reaction; J. Phys. Chem. C vol. 111 No. 5 p. 26871 (2013).
International Search Report dated Nov. 9, 2016 in counterpart App No. PCT/US2016/045595.
International Search Report dated Nov. 16, 2016 in related App. No. PCT/US2016/045603.
Related U.S. Appl. No. 15/228,904, filed Aug. 4, 2016 in the names of King and Livneh.
Lahijani, Pooya et al. "Improvement of Biomass Char-CO2 Gasification Reactivity Using Microwave Irradiation and Natural Catalyst" Thermochirnica Acta, Jan. 28, 2015(online), vol. 604, pp. 61-66.

* cited by examiner

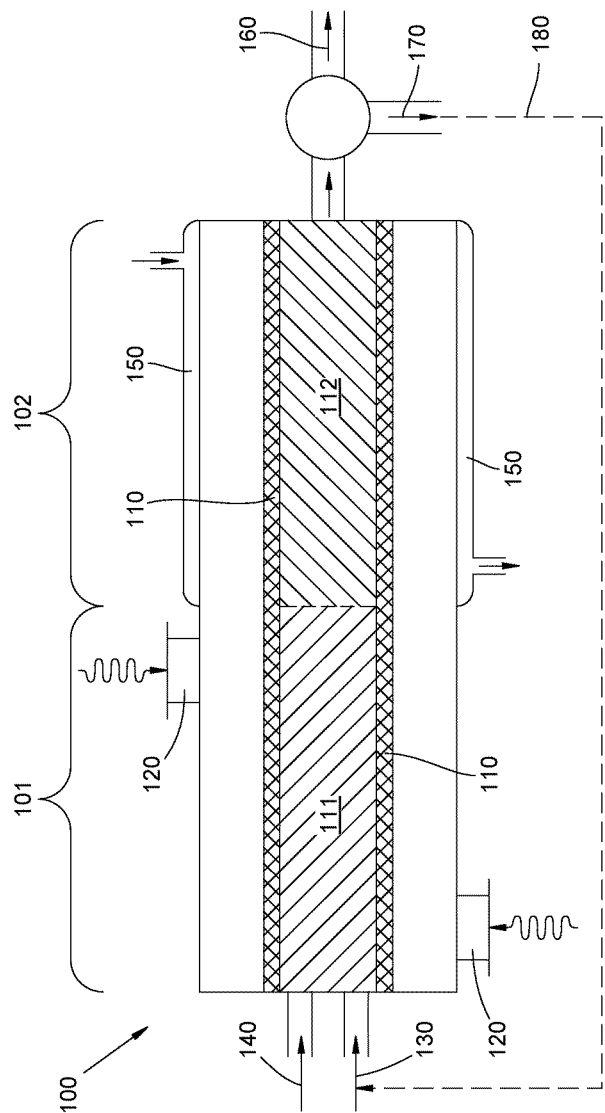

CONVERSION OF GREENHOUSE GASES BY DRY REFORMING

BENEFIT CLAIMS TO RELATED APPLICATIONS

This application claims benefit of U.S. provisional Application No. 62/202,768 entitled "Conversion of greenhouse gases by dry reforming" filed Aug. 7, 2015 in the names of Paul E. King and Ben Zion Livneh, said provisional application being hereby incorporated by reference as if fully set forth herein.

FIELD OF THE INVENTION

The field of the present invention relates to greenhouse gas conversion. In particular, conversion of greenhouse gases by dry reforming is disclosed herein.

BACKGROUND

The subject matter of the present application may be related to subject matter disclosed in:
- U.S. Pub. No. 2004/00031731 entitled "Process for the microwave treatment of oil sands and shale oils" published Feb. 19, 2004 in the names of Honeycutt et al;
- U.S. Pub. No. 2007/0004809 entitled "Production of synthesis gas blends for conversion to methanol or Fischer-Tropsch liquids" published Jan. 4, 2007 in the names of Lattner et al;
- U.S. Pub. No. 2010/0005720 entitled "Gasifier" published Jan. 14, 2010 in the names of Stadler et al;
- U.S. Pub. No. 2010/0219107 entitled "Radio frequency heating of petroleum ore by particle susceptors" published Jan. 14, 2010 in the name of Parsche;
- U.S. Pub. No. 2012/0055851 entitled "Method and apparatus for producing liquid hydrocarbon fuels from coal" published Mar. 8, 2012 in the name of Kyle;
- U.S. Pub. No. 2012/0024843 entitled "Thermal treatment of carbonaceous materials" published Feb. 2, 2012 in the names of Lissiaski et al;
- U.S. Pub. No. 2013/0303637 entitled "Method and apparatus for producing liquid hydrocarbon fuels from coal" published Nov. 14, 2013 in the name of Kyle;
- U.S. Pub. No. 2014/0051775 entitled "Method and apparatus for producing liquid hydrocarbon fuels" published Feb. 20, 2014 in the name of Kyle;
- U.S. Pub. No. 2014/0066526 entitled "Method and apparatus for producing liquid hydrocarbon fuels" published Mar. 6, 2014 in the name of Kyle;
- U.S. Pub. No. 2014/0163120 entitled "Method and apparatus for producing liquid hydrocarbon fuels" published Jun. 12, 2014 in the name of Kyle;
- U.S. non-provisional application Ser. No. 14/746,786 entitled "Method and apparatus for producing liquid hydrocarbon fuels" filed Jun. 22, 2015 in the name of Kyle;
- U.S. Pub. No. 2014/0346030 entitled "Methods and apparatus for liquefaction of organic solids" published Nov. 27, 2014 in the name of Livneh;
- U.S. Pub. No. 2014/0356246 entitled "Process and apparatus for converting greenhouse gases into synthetic fuels" published Dec. 4, 2014 in the name of Livneh;
- U.S. Pat. No. 3,505,204 entitled "Direct conversion of carbonaceous material to hydrocarbons" issued Apr. 7, 1970 to Hoffman;
- U.S. Pat. No. 4,435,374 entitled "Method of producing carbon monoxide and hydrogen by gasification of solid carbonaceous material involving microwave irradiation" issued Mar. 6, 1984 to Helm;
- U.S. Pat. No. 5,266,175 entitled "Conversion of methane, carbon dioxide and water using microwave radiation" issued Nov. 30, 1993 to Murphy;
- U.S. Pat. No. 8,779,013 entitled "Process and apparatus for converting greenhouse gases into synthetic fuels" issued Jul. 15, 2014 to Livneh;
- GB 2096635 published Oct. 20, 1982 in the name of Tao;
- WO 2008/009644 published Jan. 24, 2008 in the names of O'Connor et al;
- Fidalgo et al; "Microwave-assisted dry reforming of methane"; Intl. J. Hydrogen Energy Vol 22 p 4337 (2008);
- Fidalgo et al; "Syngas Production by $CO_2$ Reforming of $CH_4$ under Microwave Heating—Challenges and Opportunities"; Syngas: Production, Application and Environmental Impact, Indarto and Palguandi Eds. p 121 (2103); and
- Hunt et al; Microwave-Specific Enhancement of the Carbon-Carbon Dioxide (Boudouard) Reaction"; J. Phys. Chem. C Vol 111 No 5 p 26871 (2013).

Each one of those patents, publications, and applications is incorporated by reference as if fully set forth herein.

SUMMARY

A method for conversion of greenhouse gases comprises: (a) introducing a flow of a dehumidified gaseous source of carbon dioxide into a reaction vessel; (b) introducing a flow of a dehumidified gaseous source of methane into the reaction vessel; and (c) irradiating catalytic material in the reaction vessel with microwave energy. The irradiated catalytic material is heated and catalyzes an endothermic reaction of the carbon dioxide and the methane that produces hydrogen and carbon monoxide. At least a portion of heat required to maintain a temperature within the reaction vessel is supplied by the microwave energy irradiating the catalytic material. The carbon monoxide and the hydrogen can undergo catalyzed reactions producing one or more multiple-carbon reaction products in a lower-temperature portion of the reaction vessel.

Objects and advantages pertaining to dry reforming of greenhouse gases may become apparent upon referring to the example embodiments illustrated in the drawings and disclosed in the following written description or appended claims.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The drawing illustrates schematically microwave-assisted catalyzed conversion of carbon dioxide and methane to carbon monoxide and hydrogen in a higher-temperature portion of a single reaction vessel, and catalyzed conversion carbon monoxide and hydrogen into one or more multiple-carbon reaction products in a lower-temperature portion of the same reaction vessel.

The embodiments depicted are shown only schematically: all features may not be shown in full detail or in proper proportion, certain features or structures may be exaggerated relative to others for clarity, and the drawings should not be regarded as being to scale. The embodiments shown are only examples: they should not be construed as limiting the scope of the present disclosure or appended claims.

DETAILED DESCRIPTION OF EMBODIMENTS

A method, for simultaneously consuming carbon dioxide and generating one or more multiple-carbon reaction products in a single reaction vessel 100, is illustrated schematically in the drawing. A flow of a dehumidified gaseous source 130 of carbon dioxide enters the reaction vessel 100 through an input port into a higher-temperature portion 101 of the reaction vessel 100. A flow of a dehumidified gaseous source 140 of methane enters the reaction vessel 100 through an input port into the higher-temperature portion 101 of the reaction vessel 100. Although separate ports are shown, the source gas flows 130/140 could instead be combined upstream and introduced into the high-temperature portion 101 of the reaction vessel 100 through a single port.

The higher-temperature reaction vessel portion 101 contains a catalytic material 111. Any suitable catalytic material can be employed in any suitable physical form, e.g., a packed bed, coated media of any suitable shape or form, a flowing fluidized particulate catalyst, and so on. Examples of suitable catalytic materials include catalysts based on, e.g., iron, cobalt, nickel, rhodium, ruthenium, platinum, palladium, or a combination of one or more catalytic materials. In one example, the catalytic material 111 is a packed bed that includes magnetite pellets intermixed with inert alumina pellets. The catalytic material 111 in the higher-temperature reaction vessel portion 101 is irradiated with microwave energy, thereby driving an endothermic reaction (catalyzed by the material 111) of the carbon dioxide and the methane to produce hydrogen and carbon monoxide (e.g., according to the dry gas reforming reaction $CO_2 + CH_4 \rightarrow 2CO + 2H_2$; other reactions or pathways might occur as well).

In the example shown, the reaction vessel 100 contains within its volume a quartz-lined passage 110 that contains the catalytic material 111. The quartz is substantially transparent to microwaves, and so acts as windows for transmitting the microwaves to propagate into the catalytic material 111. Any suitably strong and chemically compatible material that is substantially transparent to microwave radiation can be employed as window material or to contain the catalytic material 111 and the gases 130/140 flowing through it. Examples of suitable materials can include, but are not limited to, quartz, silica, zirconia, cordierite, alumina, and so forth. The microwaves enter the reaction vessel 100 through waveguides 120. The arrangement shown in FIG. 1 is only one example of a suitable arrangement for the reaction vessel 100, microwave-transmitting windows or containment, microwave waveguides, and so forth; myriad other suitable arrangements can be implemented within the scope of the present disclosure or appended claims. In some examples, there is no space between the passage 110 and the reaction vessel 100. In some other examples, there is no distinct passage 110, and the quartz or other microwave-transmitting material is present only where microwave waveguides 120 enter the reaction vessel 100.

For a given geometry of the reaction vessel 100 and the catalytic material 111, differing numbers or arrangements of the waveguides 120 can be employed, as well as differing relative amplitudes and phases, to obtain an optimized, or at least adequate, distribution of microwave energy within the catalytic material 111 in the higher-temperature reaction vessel portion 101. In the example shown, the microwave waveguides 120 are arranged on opposing sides of the reaction vessel 100 and offset from one another along a direction of flow through the reaction vessel 100. In that example arrangement, one suitable distribution of microwave energy within the higher-temperature reaction vessel portion 101 is obtained when the phases of microwave radiation entering the reaction vessel 100 through the waveguides 120 differ from each other by about a quarter of a period of the microwave radiation (i.e., a phase difference of about $\pi/2$). Other numbers and positions of waveguides 120, and corresponding relative phases of microwave energy emerging from those waveguides, can be employed. Microwave energy at any one or more frequencies, each with one or more corresponding relative phases, can be employed that results in adequate heating of the catalytic material 111. In some examples, the microwave energy is at one or more frequencies between about 300 MHz and about 10 GHz, e.g., frequencies within the so-called industrial, scientific, and medical (ISM) radio bands; in some examples, the microwave energy is at one or more frequencies, e.g., between about 800 MHz and about 3 GHz, between about 2.4 GHz and about 2.5 GHz, between about 5 GHz and about 7 GHz, at about 915 MHz, or at about 896 MHz.

In the example shown, a lower-temperature portion 102 of the reaction vessel 100 is cooled so as to establish a suitable temperature gradient within the reaction vessel 100. The irradiated, higher-temperature portion 101 of the reaction vessel 100 exhibits a higher temperature than the cooled, lower-temperature portion 102 of the reaction vessel 100. At least a portion of heat required to maintain the temperature gradient is supplied by the microwave energy irradiating the first catalytic material 111 in the higher-temperature portion 101 of the reaction vessel 100; additional heating can be applied if need or desired. In the example shown, a cooling jacket 150 surrounds the lower-temperature reaction vessel portion 102, allowing cooling water to flow and reduce the temperature relative to the higher-temperature portion 101; cooling water can flow through any suitable arrangement of one or more jackets, pipes, coils, and so forth. Cooling of the lower-temperature portion 102 of the reaction vessel 100 can be achieved in any suitable way, including but not limited to wet or dry cooling, evaporative cooling, refrigeration, thermoelectric cooling, or cryogenic cooling.

The hydrogen and the carbon monoxide produced in the higher-temperature reaction vessel portion 101 flow from the higher-temperature portion 101 into the lower-temperature reaction vessel portion 102 containing a second catalytic material 112. As with the catalytic material 111, the second catalytic material 112 can comprise any suitable catalytic material provided in any suitable physical form, e.g., a packed bed, coated media of any suitable shape or form, a flowing fluidized particulate catalyst, and so on. In one example, the catalytic material 112 is a packed bed that includes magnetite pellets intermixed with inert alumina pellets. In fact, in the example shown there need not be any distinct boundary between the catalytic materials 111 and 112; those materials might only differ in that the material 111 is heated by microwave irradiation while the material 112 is cooled by the cooling jacket 150. In other examples there can be a distinct boundary between the two catalytic materials (e.g., by physical separation by a screen or other gas-permeable barrier, or by differing catalytic material compositions).

The second catalytic material 112 in the lower-temperature reaction vessel portion 102 catalyzes exothermic reactions involving the carbon monoxide and the hydrogen to produce one or more multiple-carbon reaction products (i.e., organic compounds containing two or more carbon atoms). The reactions occurring in the lower-temperature reaction vessel portion 102 can include myriad different reactions occurring in parallel or in sequence; many of the reactions may fall within the general category of Fischer-Tropsch processes, however, any pertinent reactions or mechanisms shall fall within the scope of the present disclosure or appended claims. A product mixture exits the reaction vessel 100 and can include unreacted (or regenerated) carbon dioxide or methane, unreacted (or regenerated) carbon monoxide or hydrogen, one or more multiple-carbon reaction products, or other reaction byproducts. At least a portion of the one or more multiple-carbon reaction products 160 can be separated from the remainder 170 of the product mixture. The one or more multiple-carbon reaction products 160 can include one or more of: (i) one or more linear or branched-chain aliphatic hydrocarbons (i.e., alkanes, alkenes, or alkynes), (ii) one or more linear or branched-chain aliphatic primary alcohols, (iii) one or more linear or branched-chain aliphatic aldehydes or ketones; (iv) one or more linear or branched-chain aliphatic carboxylic acids, (v) one or more linear or branched-chain aliphatic esters, (vi) one or more linear or branched-chain aliphatic acid anhydrides, or (vii) other multiple-carbon organic compounds.

Reaction conditions (e.g., temperatures and pressure) in both higher- and lower-temperature portions 101/102 of the reaction vessel as well as compositions and flow rates of the input reactant gas flows 130/140 can be altered or optimized to obtain various desired distributions of product compounds. For example, pressures between about 1 atm and about 30 atm can be employed; in some examples pressures between about 1 atm and about 10 atm can be employed; in some other examples pressures between about 15 atm and about 25 atm, or at about 20 atm, can be employed. In some examples in which longer-chain multiple-carbon reaction products are desired, at least a portion of the multiple-carbon reaction products (e.g., one or more shorter-chain multiple-carbon reaction products) can be separated from the mixture leaving the reaction vessel 100 and reintroduced into the reaction vessel 100 (e.g., into the lower-temperature portion 102) to undergo further reactions to produce the desired longer-chain multiple-carbon reaction products. In some of those examples, the separated multiple-carbon reaction products can be dehumidified before reintroduction into the reaction vessel 100. The chain lengths encompassed by the terms "longer-chain" and "shorter-chain" will vary according to each particular application of the disclosed methods and the particular distribution of reaction products desired from the application of those methods.

The conversion of carbon dioxide entering the reaction vessel 100 in the input gas stream 130 begins as the temperature in the higher-temperature reaction vessel portion 101 reaches about 400° C. (from heating of the catalytic material 111 by microwave irradiation; additional heating can be applied if need or desired). At that temperature, the conversion of carbon dioxide is around 40%. The carbon dioxide conversion rate increases to nearly 100% as the temperature increases from 400° C. to about 600° C. or 700° C. It is therefore useful to irradiate the catalytic material 111 only as much as necessary to maintain a temperature between about 600° C. and about 700° C. in the higher-temperature portion 101 of the reaction vessel 100; any further heating beyond about 700° C. does not improve the carbon dioxide conversion rate, but might cause excessive heating and potential damage to the catalytic material 111 or the reaction vessel 100. Temperatures between about 400° C. and about 600° C. (e.g., greater than about 475° C.) can also be maintained, albeit with correspondingly lower conversion rates of $CO_2$. Note that the elevated temperature of the catalytic material 111 can be maintained without relying on heat produced by oxidation of the methane, which would reduce the net conversion of carbon dioxide by the reaction vessel 100.

The lower-temperature portion 102 of the reaction vessel 100 is maintained at a lower temperature using the cooling jacket 150. Lower temperature conditions favor production of longer-chain products of Fischer-Tropsch processes. The cooling jacket 150 is used to keep the lower-temperature reaction vessel portion 102, and the catalytic material 112 in it, below about 350° C. Any suitable type of cooling can be employed, including but not limited to a water-cooled jacket, piping, or coils, wet or dry cooling, other coolant-based refrigeration, thermoelectric cooling, cryogenic cooling, and so forth.

The carbon dioxide source gas 130 and the methane source gas 140 are dehumidified by any suitable method (e.g., by condensation on cooling elements using wet or dry cooling, refrigerant cooling, thermoelectric cooling, or cryogenic cooling, or by using a dry or wet desiccant) to reduce or substantially eliminate water from the input gas streams 130/140. Natural gas can be employed as the methane source gas 140, and is often sufficiently dehumidified without requiring a further dehumidification process; other methane source gases might contain more water and require dehumidification before introduction as the methane source gas stream 140. Depending on the origin of the carbon dioxide source gas 130, dehumidification of the source gas 130 before introducing it into the reaction vessel 100 might be required, if the source gas 130 is not sufficiently dehumidified to begin with. Preferably, water content of the gaseous carbon dioxide source 130 and the gaseous methane source 140 is less than about 1% by volume, and the water content of the combination of all gases entering the reaction vessel 100 is less than about 3% by volume, less about 2%, or less than about 1% by volume. Within those ranges, water content can, if needed or desired, be controlled (by dehumidification) as a process parameter for controlling or optimizing the conversion of carbon dioxide. Note that the term "dehumidified" can refer to a source gas that has undergone a dehumidification process as part of the disclosed methods, or that has a sufficiently low water content as supplied without a requiring a separate dehumidification step. The degree to which one or both source gases are dehumidified can be selected, e.g., so as to achieve optimized conversion of carbon dioxide, or to achieve an acceptable level of carbon dioxide conversion while limiting the expense or energy consumption of any needed dehumidification process.

In some examples, the carbon dioxide source gas 130 is pure, or nearly pure, carbon dioxide; in many other examples, the carbon dioxide source gas 130 is not pure carbon dioxide, but will include other gases, typically inert gases. A common component of the carbon dioxide source gas 130 is nitrogen, which in some examples can be present in the carbon dioxide source gas 130 at non-zero levels up to about 80% by volume (e.g., greater than about 60% by volume, greater than about 70% by volume, or equal to about 78% by volume). The carbon dioxide conversion rates observed above were obtained at gas flow rates that resulted in residence times of the gases in the irradiated catalytic material 111 on the order of 100 milliseconds or less. The main effects of the presence of nitrogen (or other inert gas) is that it decreases the effective residence times of the carbon dioxide and methane in the catalytic material 111/112, and carries more heat away from the irradiated catalytic material 111. Both of those effects appear to be relatively minor, however. For example, higher microwave power can offset the heat carried away by the nitrogen flow.

The processes disclosed herein can be advantageously employed to convert carbon dioxide and methane, which are both potent greenhouse gases, into higher-value, multiple-carbon organic compounds, such as hydrocarbons, alcohols, aldehydes, ketones, and so forth. The processes disclosed herein can be operated so that less carbon dioxide leaves the reaction vessel 100 in the mixtures 160/170 than is introduced into the reaction vessel 100 in the source gas 130, so that a net decrease in atmospheric carbon dioxide occurs. To further reduce atmospheric carbon dioxide, at least a portion of carbon dioxide present in the mixture 170 can be recovered and reintroduced into the source gas stream 130 into the reaction vessel 100. If needed, that recovered carbon dioxide can be dehumidified (by any suitable method disclosed above) before its reintroduction into the source gas stream 130 into the reaction vessel 100.

Various plentiful sources of carbon dioxide can be employed to obtain the carbon dioxide source gas stream 130, including but not limited to combustion exhaust, biomass digestion (e.g., in the course of ethanol production), chemical processing byproducts (e.g., from hydrogen generation, production of lime or cement, ethylene production, or ammonia production), smelting or other mineral or ore processing, or any other natural or anthropogenic source of carbon dioxide. Some examples in which the carbon dioxide source gas stream 130 comprises combustion exhaust include flue gas produced by, e.g., an electrical generation facility (e.g., gas- or coal-fired) or a steam generation facility. Flue gas typically comprises about 60% or more (by volume) of nitrogen, about 10% or more (by volume) of carbon dioxide, and about 10% or more (by volume) of water vapor, with the remainder being oxygen and various trace gases (e.g., $SO_2$, $SO_3$, HCl, and so forth). Before introducing the flue gas into the reaction vessel 100 as the carbon dioxide source gas 130, it is dehumidified by any suitable process.

It has been observed that the reaction rate of carbon dioxide and methane in the higher-temperature reaction vessel portion 101 (as measured by carbon dioxide conversion) decreases over time as the reactant source gases 130/140 continue to flow into the input ports of the reaction vessel 100. It has been proposed that the decreased reaction rate might be due to so-called "coking" of the catalytic material 111 (i.e., deposition of elemental carbon on the catalytic material 111). Whatever the mechanism for the decreased reaction rate, it has also been observed that interrupting the flow of the methane source gas 140 into the reaction vessel 100 causes the carbon dioxide conversion rate to increase. A proposed mechanism for the increase is reaction of carbon dioxide in the source gas 130 with elemental carbon deposited on the catalytic material (e.g., according to the Boudouard reaction $C+CO_2 \rightarrow 2CO$). Whatever the mechanism, the methane source gas 140 can be reintroduced into the reaction chamber 100 and carbon dioxide conversion will resume at about its original rate. When the rate slows again, the interruption and resumption of methane flow can be repeated as needed to restore the reaction rate (presumably by restoration of activity of the catalytic material 111; restoration of the reaction rate by any known or unknown mechanism shall fall within the scope of the present disclosure or appended claims).

In addition to the preceding, the following examples fall within the scope of the present disclosure or appended claims:

Example 1

A method for simultaneously consuming carbon dioxide and generating one or more multiple-carbon reaction products in a single reaction vessel, the method comprising: (a) introducing a flow of a dehumidified gaseous source of carbon dioxide into a higher-temperature portion of a reaction vessel; (b) introducing a flow of a dehumidified gaseous source of methane into the higher-temperature portion of the reaction vessel; (c) irradiating first catalytic material in the higher-temperature portion of the reaction vessel with microwave energy so as to heat the first catalytic material and drive an endothermic reaction of the carbon dioxide and the methane, catalyzed by the first catalytic material, that produces hydrogen and carbon monoxide; (d) cooling a lower-temperature portion of the reaction vessel, thereby establishing a temperature gradient within the reaction vessel wherein the irradiated, higher-temperature portion of the reaction vessel exhibits a higher temperature than the cooled, lower-temperature portion of the reaction vessel, wherein at least a portion of heat required to maintain the temperature gradient is supplied by the microwave energy irradiating the first catalytic material in the higher-temperature portion of the reaction vessel; (e) allowing the hydrogen and the carbon monoxide produced to flow from the higher-temperature portion of the reaction vessel into the lower-temperature portion of the reaction vessel, wherein second catalytic material in the lower-temperature portion of the reaction vessel catalyzes exothermic reactions involving the carbon monoxide and the hydrogen to produce the one or more multiple-carbon reaction products; (f) allowing a mixture that includes the one or more multiple-carbon reaction products to flow out of the reaction vessel from the lower-temperature portion thereof; and (g) separating at least a portion of the one or more multiple-carbon reaction products from the mixture that leaves the reaction vessel.

Example 2

The method of Example 1 further comprising dehumidifying the gaseous source of carbon dioxide or the gaseous source of methane before introduction into the reaction vessel.

Example 3

The method of any one of Examples 1 or 2 wherein water content of the gaseous source of carbon dioxide and the gaseous source of methane is (i) less than about 2% by volume or (ii) less than about 1% by volume.

Example 4

The method of any one of Examples 1 through 3 wherein water content of a combination of all gases entering the reaction vessel is (i) less than about 3% by volume, (ii) less than about 2% by volume, or (iii) less than about 1% by volume.

Example 5

The method of any one of Examples 1 through 4 wherein the gaseous source of carbon dioxide includes a non-zero amount of nitrogen (i) up to about 80% nitrogen by volume, (ii) greater than about 60% nitrogen by volume, (iii) greater than about 70% nitrogen by volume, or (iv) about equal to 78% nitrogen by volume.

Example 6

The method of any one of Examples 1 through 5 wherein less carbon dioxide leaves the reaction vessel in the mixture than is introduced into the reaction vessel.

Example 7

The method of any one of Examples 1 through 6 further comprising recovering from the mixture that leaves the reaction vessel at least a portion of carbon dioxide present in that mixture, and reintroducing the recovered carbon dioxide into the higher-temperature portion of the reaction vessel.

Example 8

The method of Example 7 further comprising dehumidifying the recovered carbon dioxide before reintroduction into the higher-temperature portion of the reaction vessel.

Example 9

The method of any one of Examples 1 through 8 further comprising maintaining the reaction vessel at a temperature (i) between about 400° C. and about 600° C., (ii) above about 475° C., or (iii) between about 600° C. and about 700° C.

Example 10

The method of any one of Examples 1 through 9 further comprising maintaining the lower-temperature portion of the reaction vessel at a temperature below about 350° C.

Example 11

The method of any one of Examples 1 through 10 wherein the temperature gradient is established without relying on heat produced by oxidation of the methane.

Example 12

The method of any one of Examples 1 through 11 wherein the gaseous source of carbon dioxide comprises combustion exhaust.

Example 13

The method of Example 12 further comprising dehumidifying the combustion exhaust before introducing the combustion exhaust into the higher-temperature portion of the reaction vessel.

Example 14

The method of any one of Examples 12 or 13 wherein the combustion exhaust comprises flue gas from an electrical or steam generation facility.

Example 15

The method of any one of Examples 1 through 14 wherein the gaseous source of methane comprises natural gas.

Example 16

The method of any one of Examples 1 through 15 wherein the higher-temperature portion of the reaction vessel includes one or more windows comprising one or more materials that transmit the microwave energy, and the microwave energy irradiating the first catalytic material in the higher-temperature portion of the reaction vessel passes through the one or more windows.

Example 17

The method of any one of Examples 1 through 16 wherein the higher-temperature portion of the reaction vessel includes one or more of quartz, silica, zirconia, cordierite, or alumina.

Example 18

The method of any one of Examples 1 through 17 wherein the microwave energy is introduced into the higher-temperature portion of the reaction vessel through a pair of microwave waveguides, the microwave waveguides are arranged on opposing sides of the reaction vessel and offset from one another along a direction of flow through the reaction vessel, and phases of microwave radiation entering the reaction vessel from the waveguides differ from each other by about a quarter of a period of the microwave radiation.

Example 19

The method of any one of Examples 1 through 18 wherein the first or second catalytic material includes one or more of iron, cobalt, nickel, rhodium, ruthenium, platinum, palladium, other one or more suitable catalytic materials, or combinations thereof.

Example 20

The method of any one of Examples 1 through 19 wherein the first or second catalytic material includes magnetite.

Example 21

The method of any one of Examples 1 through 20 wherein the lower-temperature portion of the reaction vessel is cooled by a cooling water jacket, piping, or coils.

Example 22

The method of any one of Examples 1 through 21 wherein the one or more multiple-carbon reaction products includes one or more of: (i) one or more linear or branched-chain aliphatic hydrocarbons, (ii) one or more linear or branched-chain aliphatic primary alcohols, (iii) one or more linear or branched-chain aliphatic aldehydes or ketones; (iv) one or more linear or branched-chain aliphatic carboxylic acids, (v) one or more linear or branched-chain aliphatic esters, or (vi) one or more linear or branched-chain aliphatic acid anhydrides.

Example 23

The method of any one of Examples 1 through 22 further comprising separating from the mixture that leaves the reaction vessel at least a portion of the multiple-carbon reaction products present in that mixture, and reintroducing the separated multiple-carbon reaction products into the reaction vessel.

Example 24

The method of Example 23 further comprising dehumidifying the separated multiple-carbon reaction products before reintroduction into the reaction vessel.

Example 25

The method of any one of Examples 1 through 24 further comprising: (i) upon observing a decrease in a rate of carbon dioxide conversion in the reaction vessel, interrupting the flow of the gaseous source of methane into the reaction vessel, and (ii) upon observing an increase in the rate of carbon dioxide conversion in the reaction vessel after interrupting the flow of the gaseous source of methane into the reaction vessel, restoring the flow of the gaseous source of methane into the reaction vessel.

Example 26

The method of any one of Examples 1 through 25 wherein the microwave energy is at one or more frequencies: (i) between about 300 MHz and about 10 GHz; (ii) within the so-called industrial, scientific, and medical (ISM) radio bands; (iii) between about 800 MHz and about 3 GHz; (iv) between about 2.4 GHz and about 2.5 GHz; (v) between about 5 GHz and about 7 GHz; (vi) at about 915 MHz; or (vii) at about 896 MHz.

It is intended that equivalents of the disclosed example embodiments and methods shall fall within the scope of the present disclosure or appended claims. It is intended that the disclosed example embodiments and methods, and equivalents thereof, may be modified while remaining within the scope of the present disclosure or appended claims.

In the foregoing Detailed Description, various features may be grouped together in several example embodiments for the purpose of streamlining the disclosure. This method of disclosure is not to be interpreted as reflecting an intention that any claimed embodiment requires more features than are expressly recited in the corresponding claim. Rather, as the appended claims reflect, inventive subject matter may lie in less than all features of a single disclosed example embodiment. Thus, the appended claims are hereby incorporated into the Detailed Description, with each claim standing on its own as a separate disclosed embodiment. However, the present disclosure shall also be construed as implicitly disclosing any embodiment having any suitable set of one or more disclosed or claimed features (i.e., a set of features that are neither incompatible nor mutually exclusive) that appear in the present disclosure or the appended claims, including those sets that may not be explicitly disclosed herein. In addition, for purposes of disclosure, each of the appended dependent claims shall be construed as if written in multiple dependent form and dependent upon all preceding claims with which it is not inconsistent. It should be further noted that the scope of the appended claims does not necessarily encompass the whole of the subject matter disclosed herein.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open ended terminology, with the same meaning as if the phrase "at least" were appended after each instance thereof, unless explicitly stated otherwise.

In the appended claims, if the provisions of 35 USC §112(f) are desired to be invoked in an apparatus claim, then the word "means" will appear in that apparatus claim. If those provisions are desired to be invoked in a method claim, the words "a step for" will appear in that method claim. Conversely, if the words "means" or "a step for" do not appear in a claim, then the provisions of 35 USC §112(f) are not intended to be invoked for that claim.

If any one or more disclosures are incorporated herein by reference and such incorporated disclosures conflict in part or whole with, or differ in scope from, the present disclosure, then to the extent of conflict, broader disclosure, or broader definition of terms, the present disclosure controls. If such incorporated disclosures conflict in part or whole with one another, then to the extent of conflict, the later-dated disclosure controls.

The Abstract is provided as required as an aid to those searching for specific subject matter within the patent literature. However, the Abstract is not intended to imply that any elements, features, or limitations recited therein are necessarily encompassed by any particular claim. The scope of subject matter encompassed by each claim shall be determined by the recitation of only that claim.

What is claimed is:

1. A method for simultaneously consuming carbon dioxide and generating one or more multiple-carbon reaction products in a single reaction vessel, the method comprising:
   (a) introducing a flow of a dehumidified gaseous source of carbon dioxide into a higher-temperature portion of a reaction vessel;
   (b) introducing a flow of a dehumidified gaseous source of methane into the higher-temperature portion of the reaction vessel;
   (c) irradiating first catalytic material in the higher-temperature portion of the reaction vessel with microwave energy so as to heat the first catalytic material and drive an endothermic reaction of the carbon dioxide and the methane, catalyzed by the first catalytic material, that produces hydrogen and carbon monoxide;
   (d) cooling a lower-temperature portion of the reaction vessel, thereby establishing a temperature gradient within the reaction vessel wherein the irradiated, higher-temperature portion of the reaction vessel exhibits a higher temperature than the cooled, lower-temperature portion of the reaction vessel, wherein at least a portion of heat required to maintain the temperature gradient is supplied by the microwave energy irradiating the first catalytic material in the higher-temperature portion of the reaction vessel;
   (e) allowing the hydrogen and the carbon monoxide produced to flow from the higher-temperature portion of the reaction vessel into the lower-temperature portion of the reaction vessel, wherein second catalytic material in the lower-temperature portion of the reaction vessel catalyzes exothermic reactions involving the carbon monoxide and the hydrogen to produce the one or more multiple-carbon reaction products;

(f) allowing a mixture that includes the one or more multiple-carbon reaction products to flow out of the reaction vessel from the lower-temperature portion thereof; and (g) separating at least a portion of the one or more multiple-carbon reaction products from the mixture that leaves the reaction vessel.

2. The method of claim 1 further comprising dehumidifying the gaseous source of carbon dioxide or the gaseous source of methane before introduction into the reaction vessel.

3. The method of claim 1 wherein water content of the gaseous source of carbon dioxide and the gaseous source of methane is less than about 1% by volume.

4. The method of claim 1 wherein water content of a combination of all gases entering the reaction vessel is less than about 3% by volume.

5. The method of claim 1 wherein the gaseous source of carbon dioxide includes a non-zero amount of nitrogen up to about 80% nitrogen by volume.

6. The method of claim 1 wherein less carbon dioxide leaves the reaction vessel in the mixture than is introduced into the reaction vessel.

7. The method of claim 1 further comprising recovering from the mixture that leaves the reaction vessel at least a portion of carbon dioxide present in that mixture, and reintroducing the recovered carbon dioxide into the higher-temperature portion of the reaction vessel.

8. The method of claim 7 further comprising dehumidifying the recovered carbon dioxide before reintroduction into the higher-temperature portion of the reaction vessel.

9. The method of claim 1 further comprising maintaining the higher-temperature portion of the reaction vessel at a temperature above about 475° C. and maintaining the lower-temperature portion of the reaction vessel at a temperature below about 350° C.

10. The method of claim 1 wherein the temperature gradient is established without relying on heat produced by oxidation of the methane.

11. The method of claim 1 wherein the gaseous source of carbon dioxide comprises combustion exhaust.

12. The method of claim 11 further comprising dehumidifying the combustion exhaust before introducing the combustion exhaust into the higher-temperature portion of the reaction vessel.

13. The method of claim 11 wherein the combustion exhaust comprises flue gas from an electrical or steam generation facility.

14. The method of claim 1 wherein the gaseous source of methane comprises natural gas.

15. The method of claim 1 wherein the higher-temperature portion of the reaction vessel includes one or more windows comprising one or more materials that transmit the microwave energy, and the microwave energy irradiating the first catalytic material in the higher-temperature portion of the reaction vessel passes through the one or more windows.

16. The method of claim 1 wherein the higher-temperature portion of the reaction vessel includes one or more of quartz, silica, zirconia, cordierite, or alumina.

17. The method of claim 1 wherein the microwave energy is introduced into the higher-temperature portion of the reaction vessel through a pair of microwave waveguides, the microwave waveguides are arranged on opposing sides of the reaction vessel and offset from one another along a direction of flow through the reaction vessel, and phases of microwave radiation entering the reaction vessel from the waveguides differ from each other by about a quarter of a period of the microwave radiation.

18. The method of claim 1 wherein the first or second catalytic material includes magnetite.

19. The method of claim 1 wherein the lower-temperature portion of the reaction vessel is cooled by a cooling water jacket, piping, or coils.

20. The method of claim 1 wherein the one or more multiple-carbon reaction products includes one or more of: (i) one or more linear or branched-chain aliphatic hydrocarbons, (ii) one or more linear or branched-chain aliphatic primary alcohols, (iii) one or more linear or branched-chain aliphatic aldehydes or ketones; (iv) one or more linear or branched-chain aliphatic carboxylic acids, (v) one or more linear or branched-chain aliphatic esters, or (vi) one or more linear or branched-chain aliphatic acid anhydrides.

21. The method of claim 1 further comprising: (i) upon observing a decrease in a rate of carbon dioxide conversion in the reaction vessel, interrupting the flow of the gaseous source of methane into the reaction vessel, and (ii) upon observing an increase in the rate of carbon dioxide conversion in the reaction vessel after interrupting the flow of the gaseous source of methane into the reaction vessel, restoring the flow of the gaseous source of methane into the reaction vessel.

* * * * *